United States Patent [19]

Schuette

[11] Patent Number: 5,013,420
[45] Date of Patent: May 7, 1991

[54] GEL ELECTROPHORESIS/ELECTRO-BLOT APPARATUS

[75] Inventor: Michael W. Schuette, Vienna, Va.

[73] Assignee: Life Technologies Inc., Gaithersburg, Md.

[21] Appl. No.: 511,345

[22] Filed: Apr. 19, 1990

[51] Int. Cl.$^5$ .......................................... G01N 27/26
[52] U.S. Cl. ............................ 204/299 R; 204/182.1; 204/182.8
[58] Field of Search ............... 204/180.1, 182.1, 182.8, 204/299 R

[56] References Cited

U.S. PATENT DOCUMENTS

| | | | |
|---|---|---|---|
| 3,563,880 | 2/1971 | Anderson | 204/299 R |
| 3,719,580 | 3/1973 | Roberts et al. | 204/299 R |
| 3,856,655 | 12/1974 | Roberts | 204/299 R |
| 3,932,263 | 1/1976 | Brefka | 204/299 R |
| 3,947,345 | 3/1976 | Grandine et al. | 204/299 R |
| 4,416,761 | 11/1983 | Brown et al. | 204/299 R |
| 4,518,476 | 5/1985 | Delony et al. | 204/299 R |
| 4,574,040 | 3/1986 | Delony et al. | 204/182.8 |
| 4,575,040 | 3/1986 | Seely | 248/624 |
| 4,622,124 | 11/1986 | Kreisher et al. | 204/299 R |

OTHER PUBLICATIONS

*Mini-Slab by Idea Scientific*, Sales Brochure for the Mini-Slab Electrophoresis Device Manufactured by Idea Scientific Company of Corvallis, Oreg., 1 page.
*Learn to Run Faster in Five Easy Steps*, Sale Brochure for the Profile Mini Electrophoresis and Transfer System manufactured by Schleicher & Schuell of Keene, N.H., 1 page.
*A New Mighty Small Unit for Running Taller Gels*, Sales Brochure for the Tall Mighty Small SE 280 Electrophoresis Device manufactured by Hoefer Scientific Instruments of San Francisco, Calif., 1 page.
*Mini-Protean II*, Sale Brochure and Specification Sheet for the Mini-Protean II Electrophoresis Device, 3 pages.
*Analytical Biochemistry*, "A Vertical Submarine Electrophoresis Apparatus for Polyacrylamide Minigels", Spiker, S., 185:270-273, (1990).

Primary Examiner—John F. Niebling
Assistant Examiner—David G. Ryser
Attorney, Agent, or Firm—Sterne, Kessler, Goldstein & Fox

[57] ABSTRACT

A gel electrophoresis/electro-blot transfer apparatus comprising a buffer tank having a upper and lower section adapted to maintain a buffer solution, a support frame for supporting a gel slab, a first member for securing the gel slab in a substantially vertical direction in the support frame, a support frame for supporting a filter paper, gel slab, and a blotter membrane, a second member for securing the filter paper, gel slab, and membrane in intimate contact with the support frame. Assembly of the buffer tank, support frame, and securing means or the buffer tank and electro-blot support frame forms an upper buffer solution reservoir and a lower buffer solution reservoir substantially isolated from each other. The upper buffer solution reservoir and the lower buffer solution reservoir are electrically connected so that electrophoresis or electro-blot transfer can be performed.

12 Claims, 15 Drawing Sheets

Section A-A

Section B-B

Section C-C

Section D-D

GEL ELECTROPHORESIS/ELECTRO-BLOT APPARATUS

BACKGROUND OF THE INVENTION

1. Field of the Invention

The present invention relates generally to devices for performing electrophoresis and electro-blot transfer on gel slab assemblies. The present invention particularly relates to a device that can perform both vertical electrophoresis on protein and nucleic acid samples, and electro-blot transfer.

2. Related Art

Two of the most prominent techniques for separating macromolecules are chromatography and gel electrophoresis. Electrophoresis devices have evolved since the discovery that charged particles suspended between opposite poles and in an electric field migrate toward the pole possessing the charge opposite that particle.

Gel electrophoresis is primarily used to separate large macromolecules ranging in size from 1 to 10,000 KD (Kilodaltons). A kilodalton is a unit of molecular weight roughly equivalent to the mass of 1,000 hydrogen atoms. Gel electrophoresis can separate hundreds of macromolecules from one another while using less than a millionth of a gram of sample material.

Generally, the first step in conventional gel electrophoresis processes involves preparing a gel slab assembly. A gel slab is typically formed from an acrylamide solution. Typically, the acrylamide solution is cast between two glass plates separated by thin strips of plastic, (known as side spacers to those proficient in the arts). The cast acrylamide solution then polymerizes forming a pore matrix. Within the polymerized gel material, these pores form a "sieve" that retards the movement of macromolecules. Using a special comb, wells are formed at the uppermost part of the gel slab during casting. The areas below each well are termed "lanes."

Thereafter, a gel slab assembly is placed into an electrophoresis device. Samples are then placed in a narrow band within each well and an electric field is applied across the gel slab. Typically, the upper and lower portion of the gel assembly are submerged in separate isolated buffer solution reservoirs. A typical buffer solution is an SDS-Denaturing solution per Laemmli, U.K. (1970) Nature 277,680. The electric field induces the macromolecules of the samples to migrate through the gel slab. As the samples migrate, the macromolecules are "sieved" by molecular weight in their respective lanes. If the electrophoresis device is working properly, each species of macromolecules of a specific size will be in bands arranged from the top of the gel to the bottom, according to molecular weight, with the largest molecules at the top.

When performing "band" comparison between a plurality of samples, it is very important the adjacent bands represent similar macromolecules. One significant factor that controls the "band" representation from lane to lane is whether or not the electric field across the gel slab assembly is uniform. Two parameters that affect the consistency of the electric field are the current and temperature distribution across the gel slab. A non-uniform current and/or temperature distribution will cause the electric field to be stronger or weaker from one "lane" to another. As the electric field causes the macromolecules to migrate the macromolecules move down "lanes" with like macromolecules moving at different speeds if either the applied voltage or the temperature is nonuniform. These phenomena are commonly referred to as "smiles" or "frowns," with the smiling gel having the outside lanes moving slower than the central lanes, and a frown being the opposite, with the outside lanes moving faster creating the impression of a human "frown." Because visual band comparison must take place to obtain macromolecule size, and gels that are "smiling" or "frowning" are harder to compare. This is one significant problem with conventional electrophoresis devices.

As discussed earlier, the electric field is dependent on uniform current flow and uniform temperature distribution. These two parameters are intertwined. Generally, the higher the voltage applied to a given macromolecule, the faster the migration process takes place. Temperature, however, should not rise above about 60 degrees celsius, as degradation of some macromolecules will occur above this point. However, raising the voltage increases the heat generated in the gel slab. Therefore, a "trade-off" exists. Increased voltage yields desirable process times but undesirable higher gel slab temperatures and increased non-uniformity in temperature distribution.

Accordingly, with regard to current distribution, under ideal conditions, it is desirable to design a device such that the current draw is mainly through the gel slab, and not the surrounding buffer. Therefore, it is important that the positively charged and negatively charged buffer solutions be substantially isolated from each other. Conventional devices have complicated designs using rubber gaskets so as to ensure that the buffer solution reservoirs are isolated.

In addition, directing most of the current through the gel slab will decrease the overall energy dissipation. Decreased energy dissipation will reduce the overall gel slab temperature. This will ensure that the gel slab temperature is kept well below its degradation point.

With regard to temperature distribution, the problem in part, is a function of where the current is being dissipated. Therefore, a unit in which the current is non-uniform, the power will be dissipated non uniformly, causing "smiles" or "frowns." Additionally, under ideal conditions, with the current passing through the gel slab, there is a need to transfer heat from the gel to the surrounding buffer. Heat sinking the gel slab with the buffer reservoir will thereby maintain uniform temperature distribution.

Another significant problem with conventional electrophoresis devices resides in their ability to accept gel slabs of variable thickness in an unencumbered manner. This is because conventional devices are not flexible enough to easily accommodate a wide variety of gel assemblies as the complex assembly procedures, and number of parts used, hinders the user.

After electrophoresis with a non-prestained sample is performed, the samples, although present, are undetectable. Therefore, a detection technique must be utilized so that the samples can be analyzed.

One detection method involves staining and de-staining the gel slab. In this process, the entire gel slab is stained with a dye that only adheres to the macromolecules. Thereafter, a de-staining process is performed wherein dye not adhered to the macromolecules is washed away. The bands of macromolecules thus become visible.

Another common detection method involves the use of antibodies. In this method, the bands of proteins or samples are "transferred" or blotted to a macromolecule binding membrane. In order to detect the presence of certain proteins or samples on the membrane, a known antibody is introduced. The antibody will only combine with a specific protein or sample. In order to detect the antibody-protein combination, the antibodies are "tagged."

A common transfer process is called "electro-blot" transfer. In the "electro-blot" transfer process the macromolecules in the gel slab "migrate" under an electric field "on" to an electro-blot membrane. A commonly used membrane is nitrocellulose.

In designing an electro-blot transfer apparatus it is important that the blotting membrane be in close contact with the gel slab. Close contact between the gel slab and blotting membrane assures that a complete transfer of bands will occur with no significant loss of resolution. For example, the existence of air bubbles between the gel slab and blotting membrane will prevent the band images from being transferred. Additionally, like the electrophoresis devices, it is important to maintain an uniform electric field directed across the electro-blot sandwich.

In addition, preparation of the gel slab/nitrocellulose sandwich must be carefully performed so that the macromolecules on the gel membrane are not removed or contaminated. Therefore, the electro-blot apparatus must be designed so that the electro-blot sandwich can be easily assembled and disassembled.

Another problem with conventional electrophoresis and electro-blot transfer devices is that they can only perform either electrophoresis or electro-blot transfer. Having to purchase two separate units can be very costly. Furthermore, two devices can occupy more work space. This is a significant disadvantage with conventional devices.

The present invention was developed with certain objectives in mind. One objective was to develop an apparatus that could perform both electrophoresis and electro-blot transfer. Another objective was to develop an apparatus which could easily accommodate gel slab assemblies of variable thicknesses. A further objective was to develop an apparatus that would have a uniform electric field across the gel slab during electrophoresis and, using the same electrode placement, across the electro-blot sandwich during electro-blot transfer.

As will be shown below, the present invention meets the above objectives. Moreover, the present invention provides advantages heretofore unavailable in conventional devices.

SUMMARY OF THE INVENTION

The present invention comprises a buffer tank common to both the electrophoresis and electro-blot transfer processes. The buffer tank is adapted to receive a buffer solution. The buffer tank also has an upper and lower section with an electrode positioned in each section.

When performing electrophoresis, a support frame is provided for supporting one or more gel slabs. Also provided are means for securing the gel slab(s) in a substantially vertical direction in the support frame. Assembly of the buffer tank containing the buffer solution, support frame, and securing means forms an upper buffer solution reservoir and a lower buffer solution reservoir. The upper and lower buffer solution reservoirs are substantially but not completely, electrically isolated from each other.

When performing electro-blot transfer, a support frame is provided for supporting, in sequence a sandwich comprising an electro-blot pad, filter paper, gel membrane, a nitrocellulose membrane, and a second electro-blot pad. Means are also provided for securing the sandwich to the support frame. Assembly of the support frame into the buffer tank forms a first buffer solution reservoir and a second buffer solution reservoir. The first and second buffer solution reservoirs are substantially, but not completely electrically isolated from each other.

The device of the present invention also comprises means for electrically connecting the first and second buffer solution reservoirs. The electrical connecting means is common to both the electrophoresis and electro-blot transfer processes.

BRIEF DESCRIPTION OF THE DRAWINGS

The present invention will be described with reference to the accompanying drawings wherein.

DETAILED DESCRIPTION OF THE PREFERRED EMBODIMENTS

The electrophoresis/electro-blot transfer apparatus of the present invention provides advantages and capabilities heretofore unavailable in conventional gel slab devices. Although the preferred embodiment will be now described, it will be appreciated by those skilled in the electrophoresis and/or electro-blot arts, that the present invention can be fabricated in a number of ways without departing from the inventive concept.

The present invention will be described with reference to two embodiments; the electrophoresis embodiment and the electro-blot transfer embodiment.

I. Electrophoresis embodiment

Figure 1:
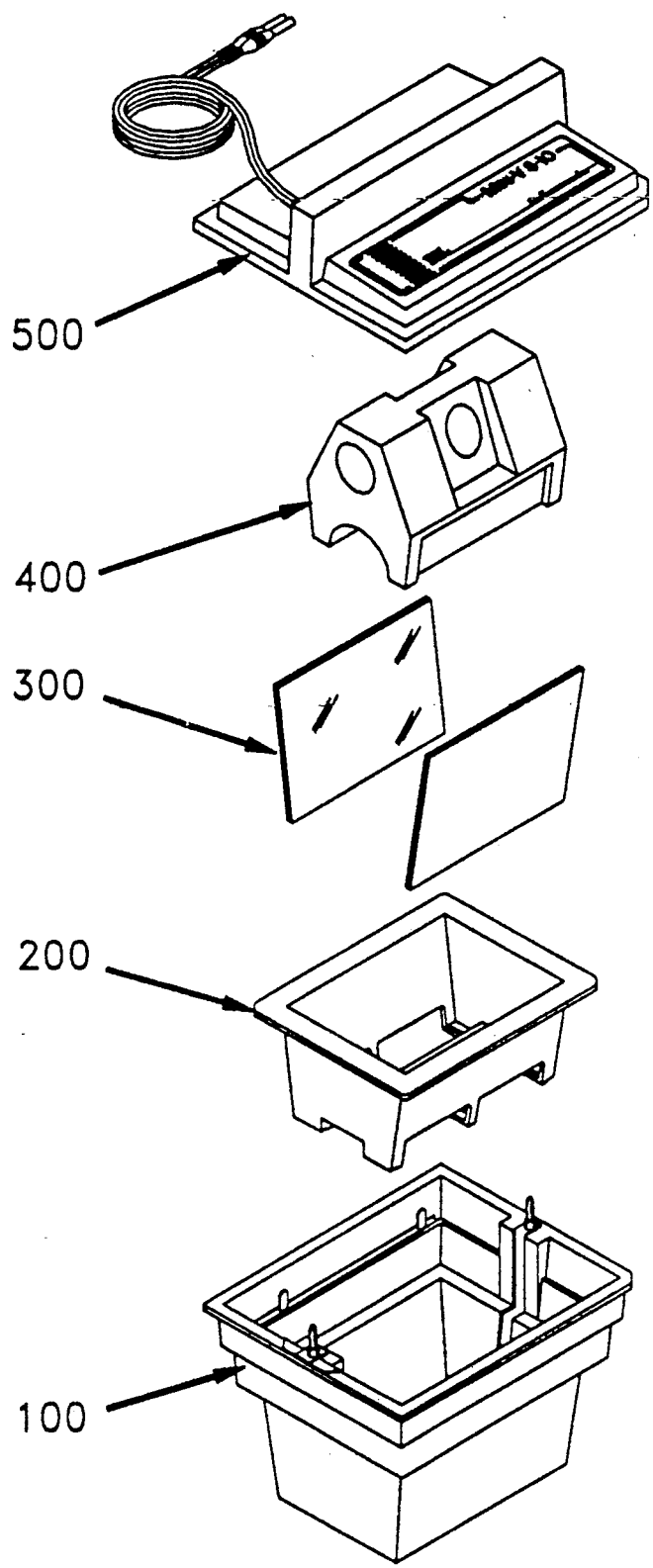
FIG. 1 shows an exploded view of the electrophoresis embodiment of the present invention.

FIG. 1 shows the main features of the electrophoresis embodiment. The electrophoresis embodiment generally comprises a buffer tank 100 (which, as will be discussed, is common to both the electrophoresis and electro-blot transfer processes), a support frame 200, a plurality of gel slabs assemblies 300, a clamping block 400, and a cover 500 (which, as will also be discussed, is common to both the electrophoresis and electro-blot transfer processes).

Figure 2:
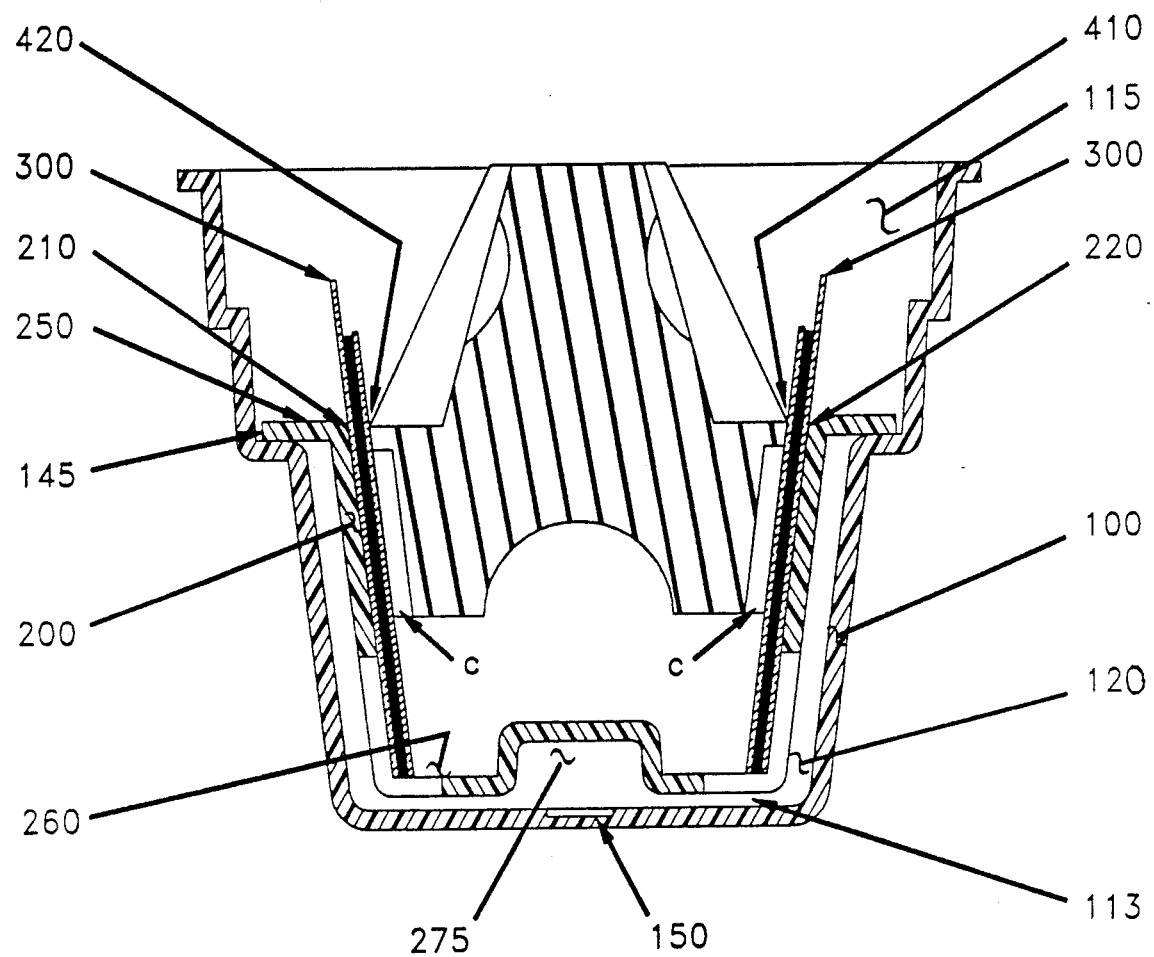
FIG. 2 shows a cross-sectional assembly view of the electrophoresis embodiment of the present invention.

FIG. 2 depicts the operational relationship between the main features of the electrophoresis embodiment. Each of the main features identified by FIG. 1 will now be described in detail as to its construction and operational relationship with the other main features. Throughout this description, FIG. 2 will be utilized to assist in understanding the operational relationship between the main features of the electrophoresis embodiment.

Figure 3A:
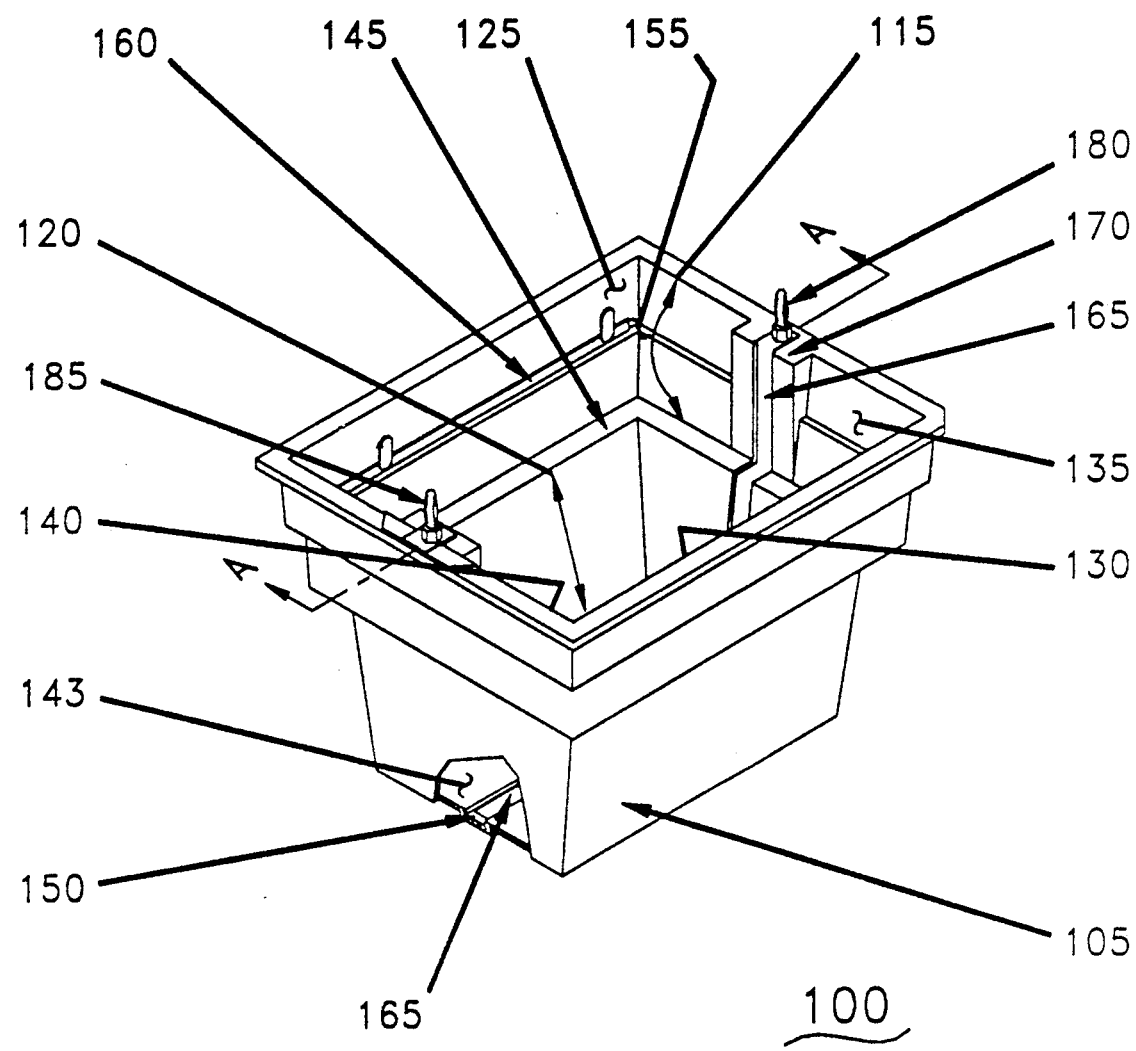
FIG. 3(a) shows a perspective view of the buffer tank for both the electrophoresis and electro-blot embodiments.

Referring to FIG. 3(a), common buffer tank 100 comprises a buffer tank body 105. Buffer tank body 105 is formed to have a first inside sidewall 125, a second inside sidewall 130, a first inside end wall 135, and a second inside end wall 140. Buffer tank body 105 also has a ledge 145. As can be seen from FIGS. 1 and 2, ledge 145 provides a bearing surface for support frame 200 during electrophoresis. Ledge 145 also serves to separate buffer tank 100 into an upper section 115 and a lower section 120.

Buffer tank body 105 further has a floor 143. Floor 143 has a recessed groove 150 formed therein. Recessed groove 150 continuously extends to and up first inside end wall 135. Recessed groove 150 is formed so as to accept an electrically conductive electrode strip 165. Although in the preferred embodiment a narrow rectangular shape is shown, electrode strip 165 may be made in a variety of shapes and thicknesses. For example, conductive electrode strip could be a small diameter wire. One factor driving the shape and thickness characteristic is the amount of current required to drive the electrophoresis process and the need to maintain a constant flux density. Electrode strip 165 is preferably made from platinum-niobium. Electrode strip 165, however, can be made from stainless steel (316), or platinum-niobium, platinumtitanium, or platinum wire.

Electrode strip 165 is formed with a slight bow so that its internal resiliency will secure it to recessed groove 150. However, a variety of other means exist for fastening electrode strip 165 to recessed groove 150. For example, electrode strip 165 could be attached by an appropriate dielectric adhesive or screwed into recessed groove 150, although care must be taken to avoid short-circuit problems.

Buffer tank 100 also comprises a first electrode adaptor 180. Electrode adaptor 180 of the preferred embodiment is a "male" type adaptor. The male electrode adapters are of the type commonly known as "banana plugs." As best seen from FIG. 3(b), electrode adaptor 180 has a lower threaded portion 182 which passes through openings in both electrode strip 165 and the top of inside end wall 135. Lower threaded portion 182 is adapted to receive a standard nylon nut 170. Fastening of nut 170 to lower threaded portion 182 ensures that good electrical contact exists between electrode adaptor 180 and electrode strip 165.

Buffer tank 100 is further formed with an upper electrode mounting lip 155 for receiving a second electrode strip 160. Electrode strip 160 has the same form and properties as does electrode strip 165. Electrode strip 160 extends along inside sidewall 125 and on mounting lip 155 to and up the center of second inside end wall 140. Electrode strip 160 terminates at the top of second inside end wall 140. Electrode strip 160 is fastened to inside sidewall 125 using polycarbonate (Lexan ®) tabs 195. Tabs 195 are fastened using an adhesive compatible with a polycarbonate material.

Figure 3B:
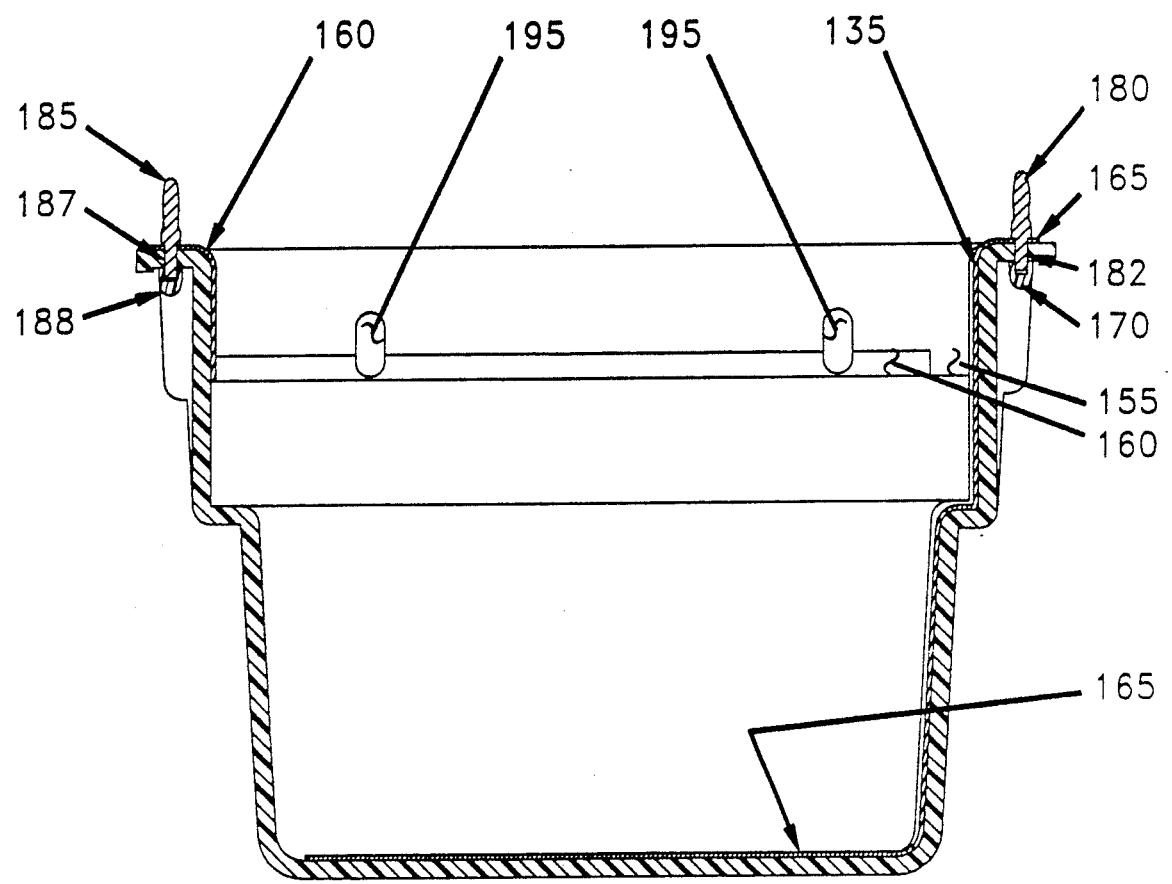
FIG. 3(b) shows a sectional view of FIG. 3(a) taken along line A—A.

Buffer tank 100 also comprises a second electrode adaptor 185. Second electrode adaptor 185 of the preferred embodiment, like electrode adaptor 180, is a male type adaptor. Electrode adaptor 185 of the preferred embodiment is the same as electrode adaptor 180. As shown in FIG. 3(b), electrode adaptor 185 also has a lower threaded portion 187 which passes through openings in both conductive strip 160 and the top of second inside end wall 140. Lower threaded portion 187 is securely fastened by a nylon nut 188 so that good electrical contact exists between electrode adaptor 185 and conductive strip 160.

In the preferred embodiment, buffer tank body 105 is a one piece cavity fabricated by a "pressure-forming" process. Pressure-forming is well known in the art. Buffer tank body 105 is preferably made from polycarbonate (Lexan ®).

Buffer tank body 105, however, can be made from a number of materials and fabricated in a number of ways. For example, buffer tank body 105 could be made from separate pieces or by an injection molding process. Buffer tank body 105 can also be formed in different shapes than those described above. For example, buffer tank body could be formed in a circular shape as opposed to a rectangular or square shape.

Figure 4A:
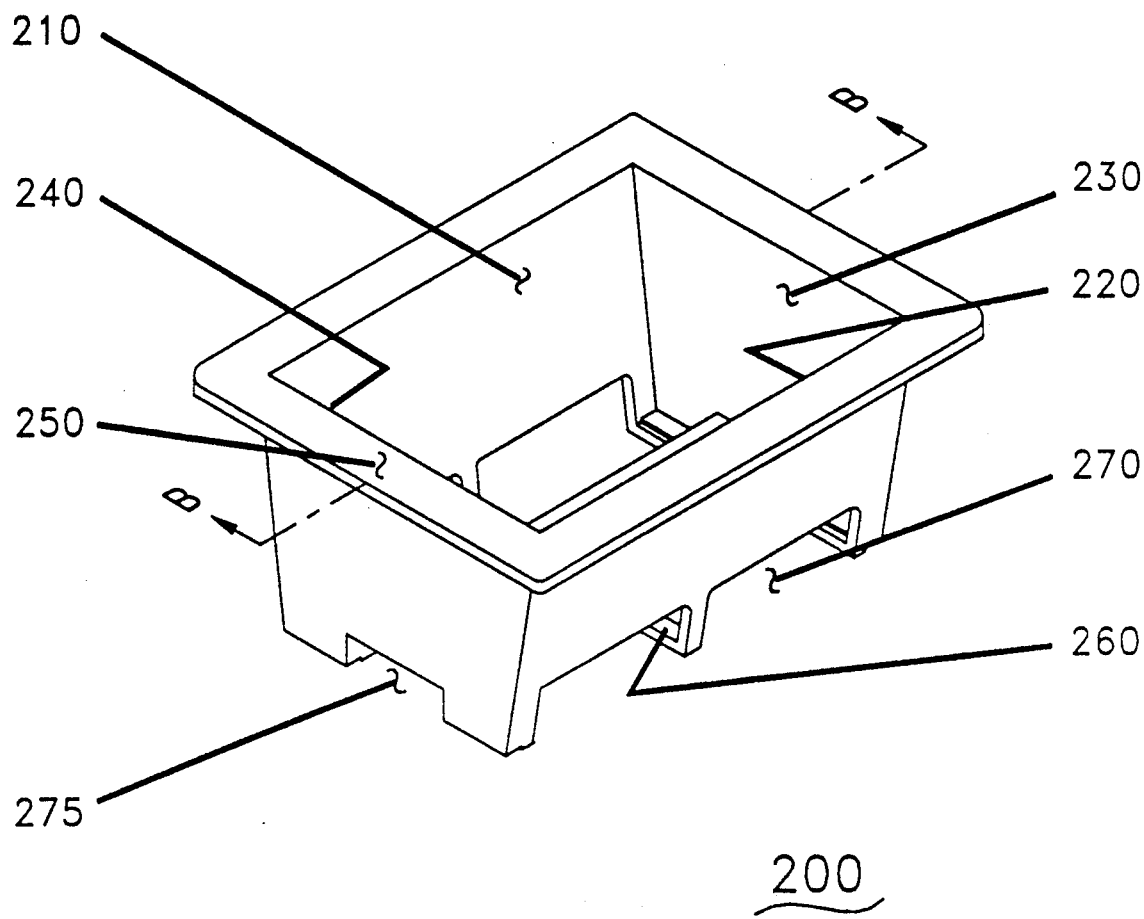
FIG. 4(a) shows a perspective view of the support frame.

As shown in FIG. 4(a), support frame 200 has a first inside sidewall 210 and a second inside sidewall 220. As can be seen from FIG. 2, first inside sidewall 210 and second inside sidewall 220 provide a bearing surface for one surface of gel slab assemblies 300. Support frame 200 also has a first inside end wall 230 and a second inside end wall 240. Support frame 200 further has a flange lip 250. As can be seen from FIG. 2, when support frame 200 is assembled, flange lip 250 rests on ledge 145 of buffer tank 100.

Figure 4B:
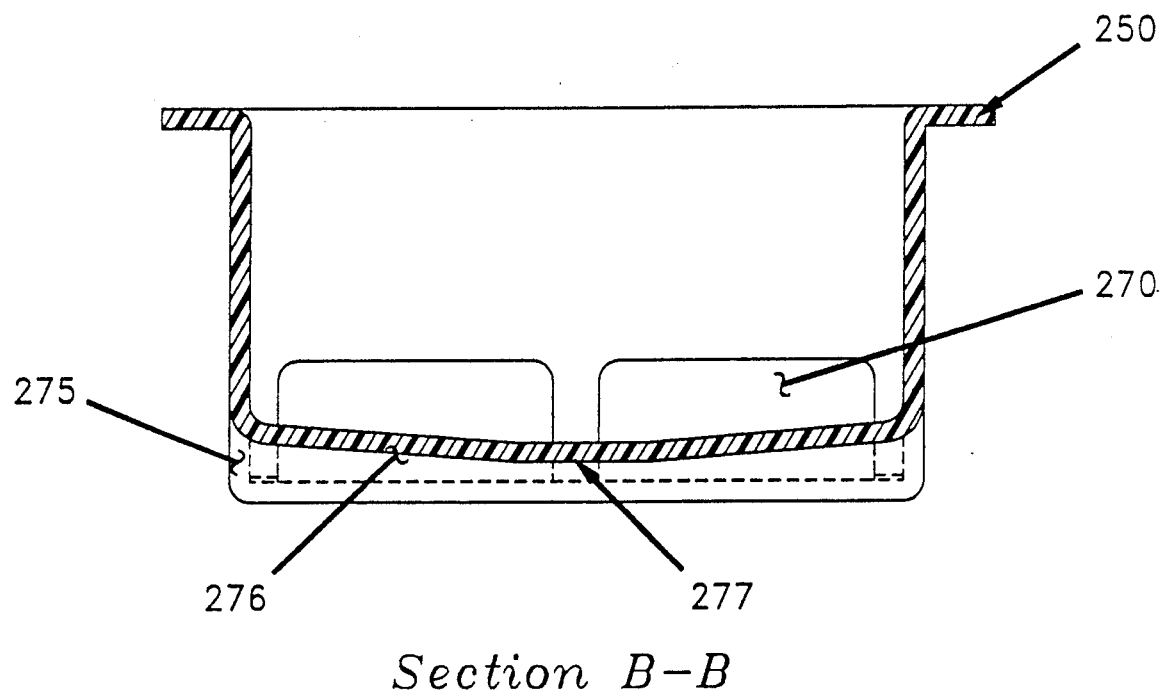
FIG. 4(b) shows a sectional view of FIG. 4(a) taken along line B—B.

As shown in FIG. 4(b), support frame 200 further includes a ribbed floor 260. Ribbed floor 260 is provided to insure that sidewalls 210 and 220 do not flex outward during operation. Furthermore, openings 270 are formed so that the bottom portion of gel slab assemblies 300 will be exposed to the buffer solution.

Support frame 200 is also formed with a recessed channel 275. As shown in FIG. 4(b), recessed channel 275 is designed so as to have a taper 276 which has a maximum peak 277 at its center. Taper 276 allows recessed channel 275 to vent the air bubbles, given off by the electrophoresis process, up to flange lip 250/ledge 145 interface. The air bubbles increase the sealing contact at the flange lip 250/ledge 145 interface to thereby increase isolation between the upper and lower buffer solution reservoirs.

Support frame 200 is made from polycarbonate and fabricated by a "pressure-forming" process. Support frame 200, however, can be made from a variety of materials and fabricated in a number of ways. Support frame 200 can also be formed in configurations other than those described above. For example, support frame 200 could be formed without a ribbed floor 260, thus leaving the bottom portion of support frame 200 completely exposed to the buffer solution. Likewise, support frame 200 could be formed with a floor having circular openings which would also expose the bottom of gel assemblies 300 to the buffer solution.

Figure 5A:
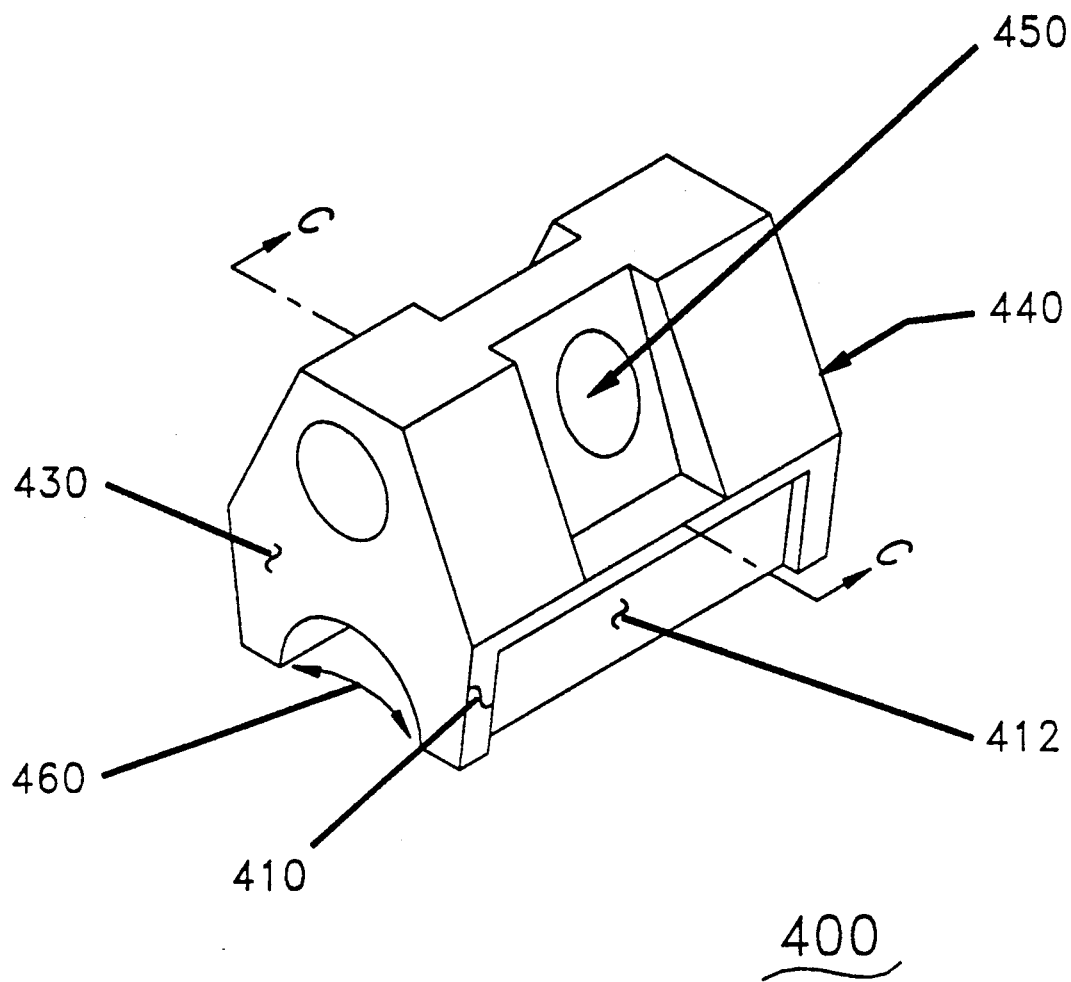
FIG. 5(a) shows a perspective view of the clamping block.
Figure 5B:
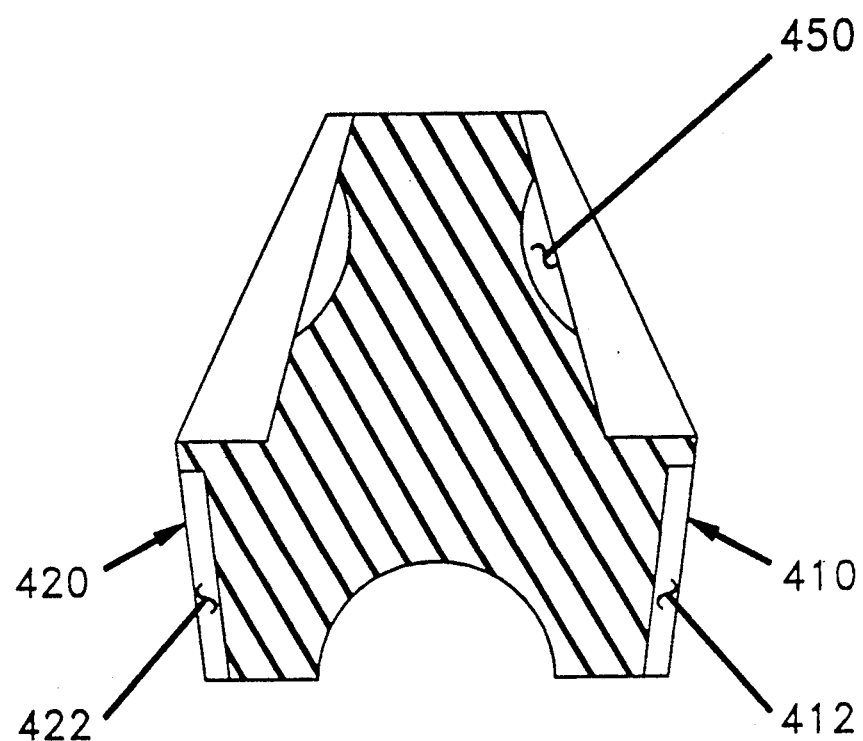
FIG. 5(b) shows a cross sectional view of FIG. 5(a) taken along line B—B.

Clamping block 400 (FIG. 5(a)) and FIG. 5(b) is formed to have a first sloped sidewall surface 410 and a second sloped sidewall surface 420. Sloped sidewall surfaces 410 and 420 are provided so that a variety of gel assembly thicknesses can be accommodated. As best shown by FIG. 2, sloped sidewall surfaces 410 and 420 secure gel assemblies 300 against first inside sidewall 210 and second inside sidewall 220 of support frame 200. Sloped sidewall surfaces 410 and 420 also make installation and removal easier.

As best depicted in FIG. 5(b), sloped sidewall surface 410 and 420 have a first recessed area 412 and a second recessed area 422, respectively. As shown by FIG. 2, first and second recessed areas 412 and 422 provide a channel C between the lower buffer solution reservoir and the upper portion of gel assemblies 300. This increased contact area allows the buffer solution reservoir to act as a heat sink so that the gel assemblies 300 will have a uniform temperature.

Clamping block 400 further has a first end wall 430 and second end wall 440. A gripping area 450 is also provided so that clamping block 400 can be easily handled. Clamping block 400 also has a third recessed area 460. As shown in FIG. 2, a third recessed area 460 is provided so that clamping block 460 will fit over channel 275 of support frame 200. Recessed area 460 also provides flexibility and resilience to clamping block 400 so that first sloped sidewall surface 410 and second sloped sidewall surface 420 can move inwardly.

Clamping block 400 is made from a urethane based material and processed to have a low durometer (40-60 on Shore A scale). Clamping block 400 is formed by a casting process. Clamping block 400, however, can be made from a variety of materials and fabricated in a number of ways. The shape and design of clamping block 400 may also take configurations other than those described above.

Figure 6A:
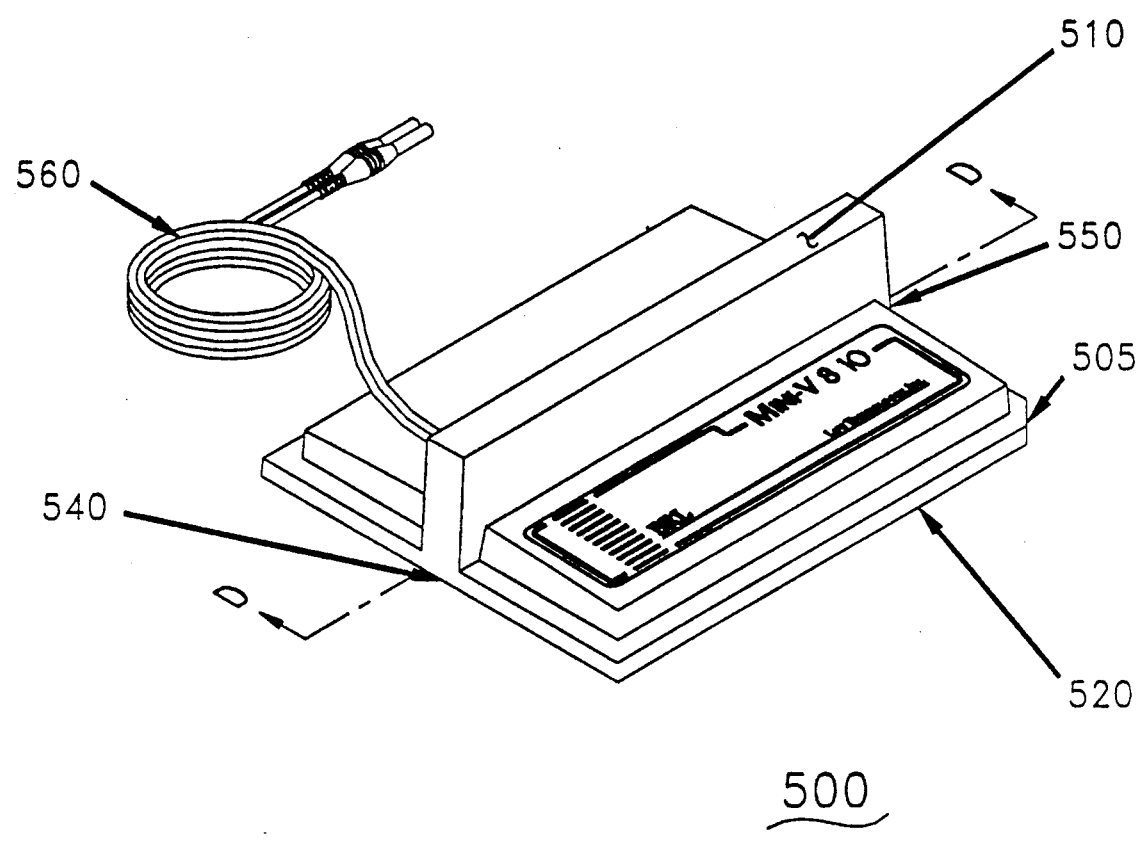
FIG. 6(a) shows a perspective view of the cover.
Figure 6B:
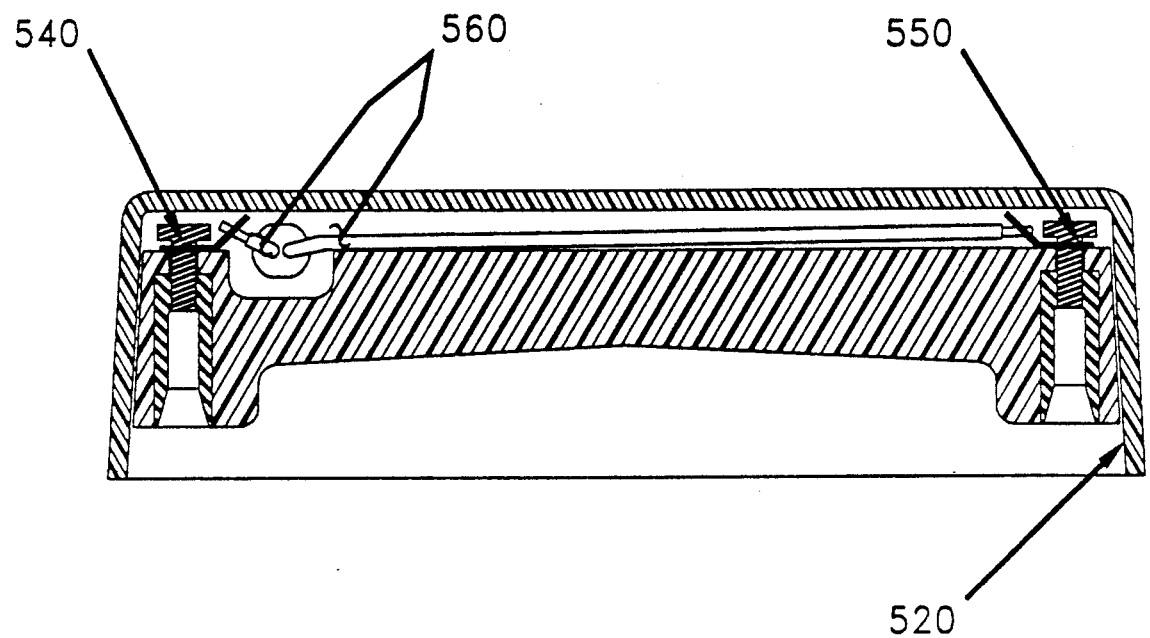
FIG. 6(b) shows a cross-sectional view of FIG. 6(a) taken along line C—C.

As shown in FIGS. 6(a) and 6(b), cover 500 comprises a cover body 505 formed to have a handle 510 and recessed lip 520. Recessed lip 520 is formed so as to mate with the 45 degree chamfer on the top of buffer tank 100, this insures proper electrical connection during operation. As shown in FIG. 6(b), cover 500 also comprises first and second electrode adapters 540 and 550, respectively. First and second electrode adapters 540 and 550 are "female" type connectors. Female electrode adapters are of the type commonly known as a "banana jacks."

When cover 500 is assembled onto buffer tank 100, electrode adaptor 540 engages with electrode adaptor 185 of buffer tank 100. Likewise, electrode adaptor 550 engages electrode adaptor 180.

Cover 500 further comprises a plurality of electrical cables 560. Electrical cables 560 are provided so that electrode adapters 550 and 540 can be connected to a negative and positive power source respectively. One end of electrical cables 560 are "hard-wired" to first and second electrode adapters 540 and 560. The other end of electrical cable 560 connects to a power supply (not shown).

Cover 500 is made from an ABS plastic based material. Cover 500 is initially formed by a "pressure-forming" process. Thereafter, cover 500 is machined to meet the above identified features. Cover 500, however, can be made from a variety of materials and fabricated by a number of techniques. Cover 500, can also have various shapes and configurations. For example, cables 600 could be situated such that they exit the top of cover 500. Likewise, handle 510 could be adapted to work with automated machinery. For example, cover 500 could have a handle shaped to have a recess upon which a robotic arm could grasp.

2. Electro-blot transfer embodiment

Figure 7:
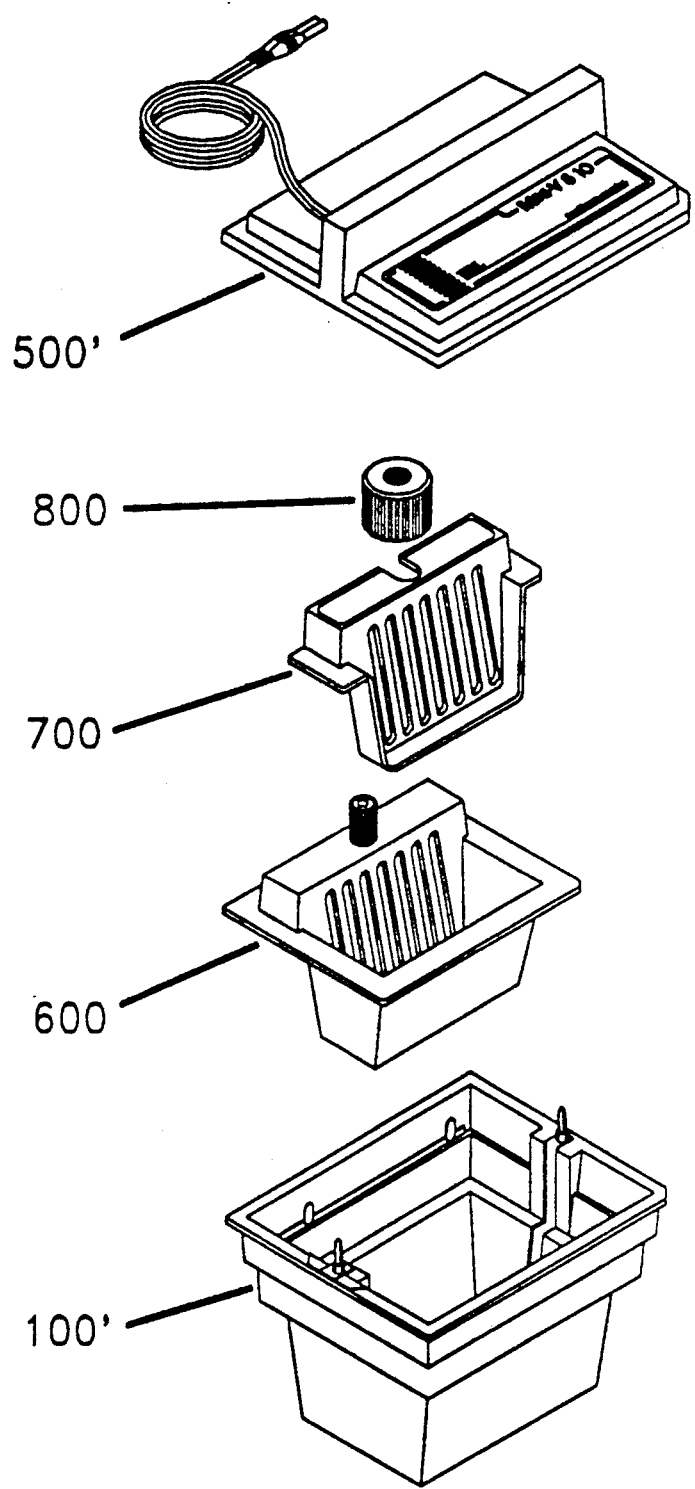
FIG. 7 shows an exploded view of the electro-blot transfer embodiment of the present invention.

The electro-blot transfer embodiment will now be described. As shown in FIG. 7, the electro-blot transfer embodiment comprises a tank 100', an electro-blot support frame 600, an electro-blot restrainer 700, a clamping knob 800 and a cover 500'. Tank 100' and cover 500' are the same components as described in the electrophoresis embodiment (tank 100 and cover 500). This redundant feature is one significant attribute of the present invention.

Figure 8:
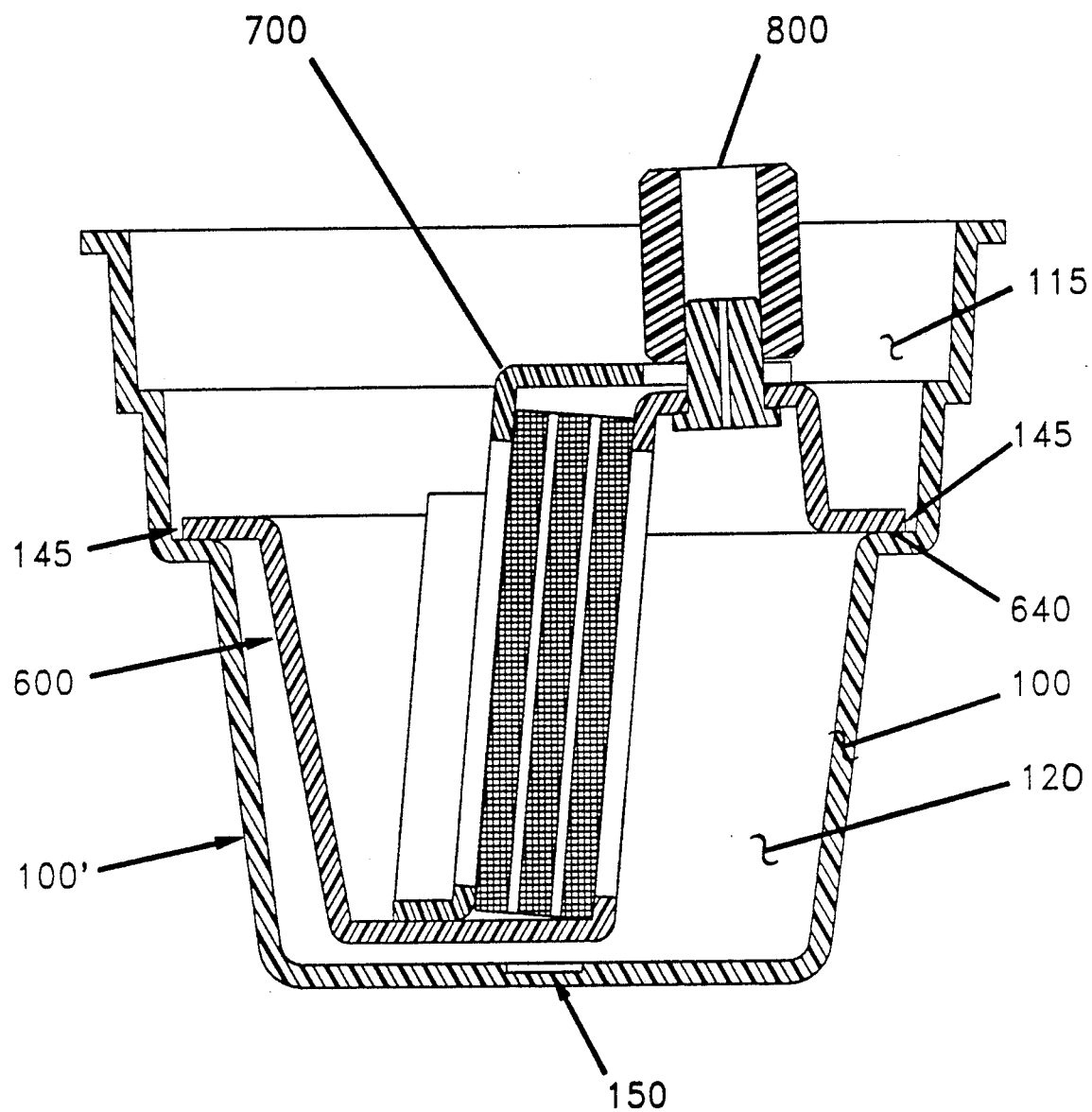
FIG. 8 shows a cross-sectional view of an assembled electro-blot transfer embodiment.

FIG. 8 depicts the operational relationship between main features of the electro-blot transfer embodiment. Each of the main features identified in FIG. 7 will now be described in detail as to its construction and operational relationship with the other main features. Throughout this description, FIG. 8 will be utilized to assist in understanding the operational relationships.

Figure 9:
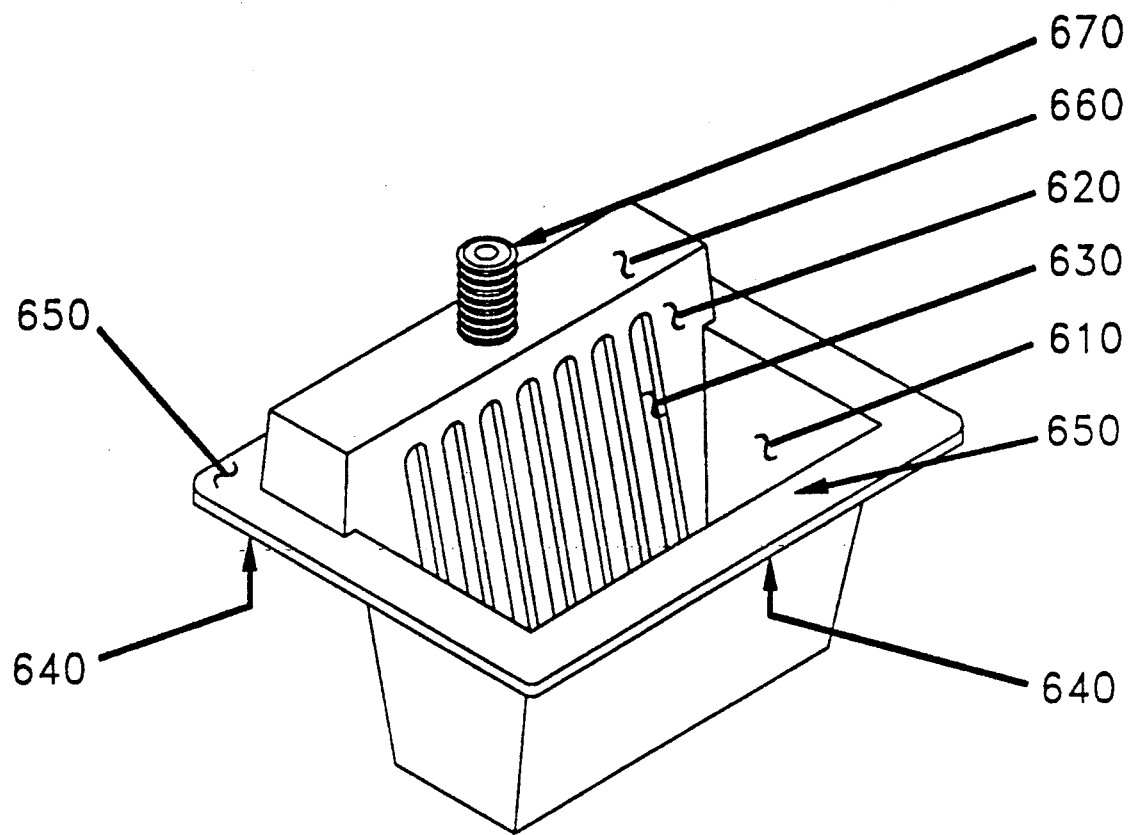
FIG. 9 shows a perspective view of the electro-blot support frame.

Referring to FIG. 9, electro-blot support frame 600 has an inside cavity 610 and a support surface 620. Support surface 620 is formed with a plurality of vertical slots 630. Electro-blot support frame 600 also has a lower flange lip surface 640 and an upper flange lip surface 650. As can be seen from FIG. 8, when assembled, lower flange lip surface 640 rests on ledge 145 of buffer tank 100. Electro-blot support frame 600 also has a support surface 660 formed therein for mounting a fixed clamping screw 670.

Support frame 600 is preferably made from polycarbonate (Lexan ®). Support frame 600 is initially formed by a "pressure-forming" process. Support frame 600 is subsequently machined to form the above identified features. Support frame 600, however, can be made from a variety of materials and fabricated by a number of processes. Support frame 600 can also have different shapes other than those described above.

Figure 10:
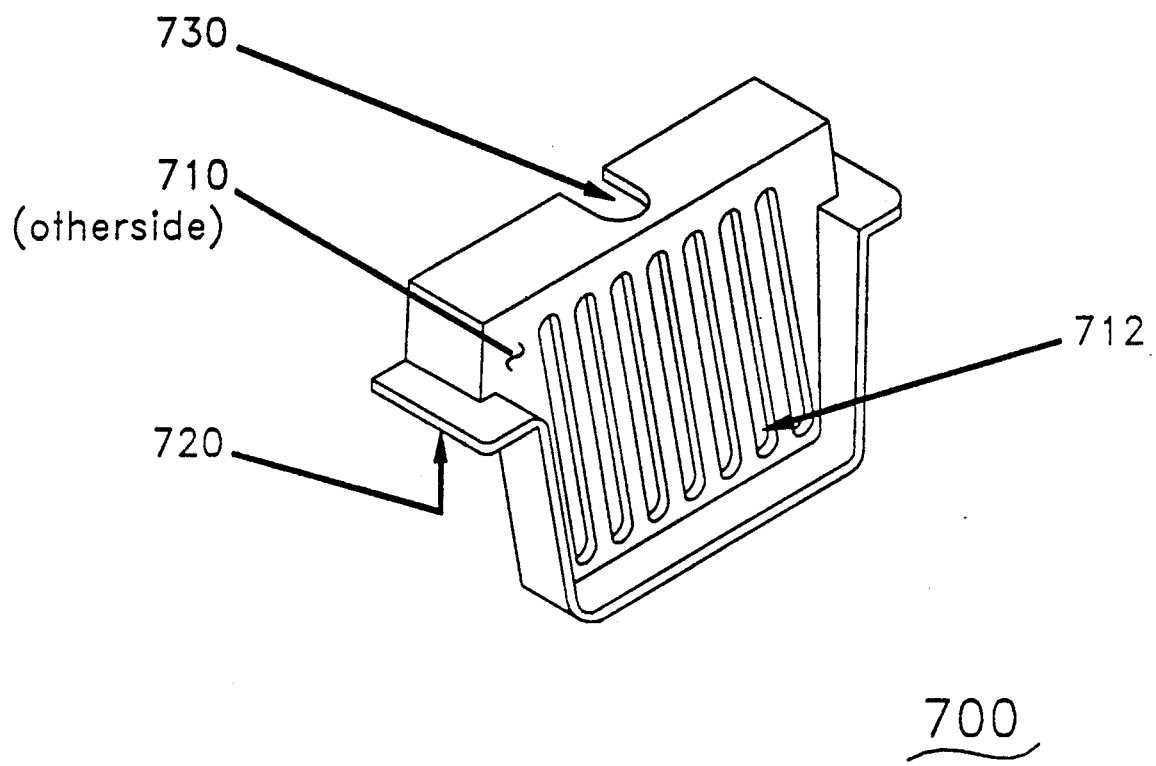
FIG. 10 shows a perspective view of the electro-blot restrainer.

FIG. 10 shows a perspective view of electro-blot restrainer 700. As shown, electro-blot restrainer 700 is formed to have a support surface 710, a flange lip surface 720 and a U-recess slot 730. As can be seen from FIG. 8, electro-blot restrainer 700 is assembled to electro-blot support frame 600 via clamping knob 800. When assembled, flange lip surface 720 is in contact with upper flange lip surface 650 of electro-blot support frame 600. Support surface 710 also has a plurality of vertical slots 712 formed therein. When assembled, it is important to make sure that the vertical slots 712 of support surface 710 are in registration with the vertical slots 630 of support frame 600.

Electro-blot restrainer 700 is preferably made from polycarbonate (Lexan ®). Electro-blot restrainer 700 is initially formed by a "pressure-forming" process. Electro-blot restrainer 700 is subsequently machined to form the above identified features. Electro-blot restrainer 700, however, can be made from a variety of materials and fabricated by a number of processes. Support frame 600 can also have different shapes other than those described above.

The preferred method of using the electrophoresis and electro-blot transfer embodiments will now be explained.

A plurality of gel slab assemblies are formed using conventional techniques. Thereafter, the apparatus of the present invention is assembled in either an electrophoresis configuration or an electro-blot transfer configuration.

As shown in FIG. 2, when performing electrophoresis gel slab assemblies 300 are placed into support frame 200 with gel slab assemblies 300 pressed against first inside sidewall 210 and second inside sidewall 220. Clamping block 400 is then placed into support frame 200. When assembled, gel assemblies 300 lie flat against first inside sidewall 210 and second inside sidewall 220. In addition, the bottom of gel slab assemblies 300 touch floor 260 of support frame 200. Thereafter, buffer solution is added to buffer tank 100. The buffer solution of the electrophoresis embodiment is typically made to conform to that of Laemmli, U.K. (1970) Nature 277,680. Support frame 200 is then placed into buffer tank 100. Displacement of the buffer solution caused by insertion of support frame 200 causes the buffer solution to rise above electrode strip 160 (shown in FIG. 3). Accordingly, two buffer solution reservoirs are then formed. Thereafter, samples are inserted into the wells of gel assemblies 300 using a conventional syringe or micropipette. Cover 500 is then placed on buffer tank 100, and cables 560 are connected to a power supply, with a typical run taking place at about 100v 100ma for 20 min. The gels slabs are now ready to be processed.

When performing electro-blot transfer, gel slabs 300 are first equilibrated in a transfer buffer so that unwanted salt and detergents from the electrophoresis buffer are removed. The electro-blot transfer buffer is a solution made typically of Tris Hcl, Methanol and sodium dodecylsulfate. If the gel slabs 300 are not equilibrated, electro-blotting will generate excess heat due to the conductivity of the salt. In addition, gel slabs 300 of less than 12% acrylamide will shrink during electro-blotting due to the presence of methanol in the buffer.

Figure 11:
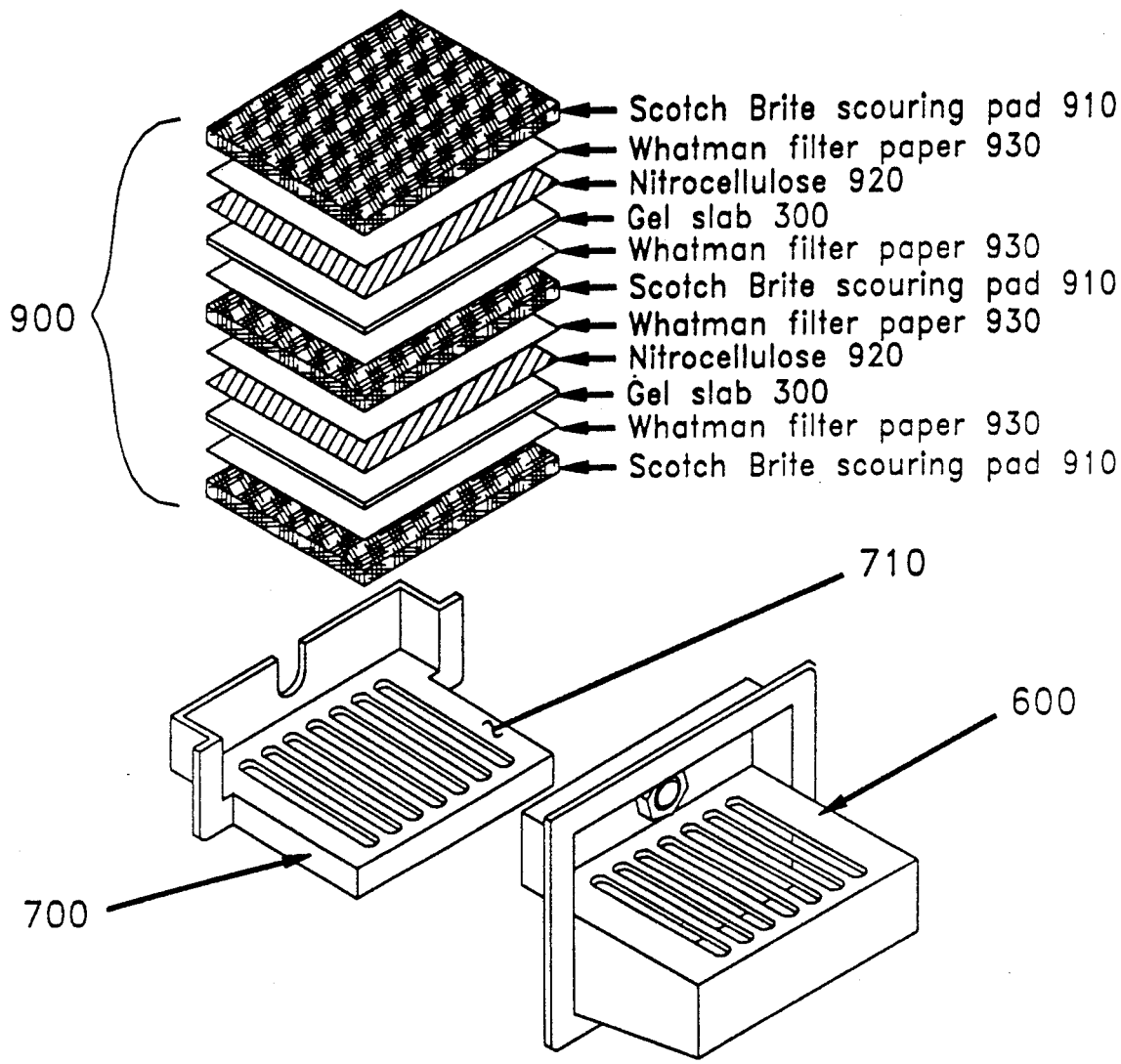
FIG. 11 shows an exploded view of the electro-blot sandwich assembled in conjunction with the electro-blot support frame and restrainer.

An electro-blot sandwich 900 is then prepared for electro-blotting of two gel slabs 300. FIG. 11 shows an exploded view of an electro-blot sandwich 900 for electro-blotting two gel slabs 300. Electro-blot sandwich 900 comprises two gel slabs 300, three pieces of electro-blot pads 910 (e.g., Scotchbrite pads), two pieces of blotting membrane 920 (nitrocellulose) and four pieces of filter paper 930 (chromatography grade). For electro-blotting only one gel, electro-blot sandwich 900 would comprise one gel slab 300, 2 electro-blot pads 910, two filter papers 930, and one blotting membrane 920.

Thereafter, assembly of the electro-blot sandwich in the present invention is performed. Electro-blot restrainer 700 is placed in a glass baking dish (not shown) containing transfer buffer with the opposite side of support surface 710 forming a platform on the bottom of the dish. As shown in FIG. 11, one pre-soaked electro-blot pad 910 is first centered on support surface 710 of re-strainer 700. A piece of filter paper 930 is then stacked on top of the pad. Gel slab 300 is then centered on filter paper 930. It is important to make sure that no bubbles have been trapped between gel slab 300 and filter paper 930. Blotting membrane 920 is then placed on gel slab 300. Likewise, it is also important to make sure that no bubbles are trapped between the gel slab 300 and blotting membrane 920. A second piece of filter paper 930 is then placed on top of blotting membrane 920, followed by another electro-blot pad 930. The above sequence is the same for the second gel slab 300.

Tank 100' is filled with approximately 1 liter of prechilled (4° C.) electro-blot transfer buffer. Electro-blot restrainer 700 is then assembled and secured with electro-blot support frame 600 using clamping knob 800. As shown by FIG. 8, the electro-blot restrainer 700/electro-bolt support frame 600 sub-assembly is then placed into buffer tank 100. Cover 500 is then attached to tank 100, thus forming a first reservoir and a second reservoir. Cables 560 are then connected to a power supply. The transfer process is now ready to begin.

As should be apparent from the above detailed description, the present invention provides significant advantages over conventional electrophoresis and electro-blot devices. The present invention allows the electrophoresis and electro-blot transfer processes to be performed in the same buffer tank using the same electrodes. This feature reduces the amount and expense of the apparatus required. Moreover, the present invention allows substantially vertical electrophoresis to be conducted while at the same time being flexible to accommodate gel slab assemblies of variable thicknesses. Furthermore, when assembled, the present invention design forms two isolated buffer solution reservoirs without gaskets or sealing agents such as grease or argarose, reducing the current draw. In addition, the present invention creates uniform electric fields, thereby simplifying interlane comparisons.

The foregoing description in intended primarily for purposes of illustration. The present invention may be embodied in other forms or carried out in other ways without departing from the spirit or scope of the invention. The present embodiment is therefore not to be considered restricted to the particular structure or operational features described above. Modifications and variations still falling within the spirit or scope of the present invention will be readily apparent to those skilled in the art.

What is claimed is:

1. Apparatus for analyzing chemical compositions using gel slabs or gel slab assemblies, comprising:
   a buffer tank having a single buffer solution reservoir;
   a support frame for supporting at least one gel slab, said support frame being mountable in said buffer tank;
   means for securing the at least one gel slab in said support frame;
   wherein, when said support frame and said securing means are mounted in said buffer tank, said frame, said securing means and said buffer tank create and define a first and second reservoir from said single buffer solution reservoir;
   first and second electrodes located in said first and second buffer solution reservoirs, respectively; and
   means for connecting said first and second electrodes to a power source.

2. Apparatus according to claim 1, wherein said securing means and said support frame act to position the at least one gel slab in a substantially vertical direction.

3. Apparatus according to claim 2, wherein said securing means comprise a wedge block for wedging the at least one gel slab into engagement with said support frame.

4. Apparatus according to claim 3, wherein said wedge block has first and second sloped surfaces for wedging the at least one gel slab into engagement with said support frame.

5. Apparatus according to claim 4, further comprising means for controlling the temperature of the at least one gel slab assembly.

6. Apparatus as claimed in claim 5, wherein said temperature control means comprises a channel between said first reservoir and the at least one gel slab.

7. Apparatus according to claim 6, wherein said connecting means comprises a cover having third and fourth electrodes, wherein when said cover is positioned on said buffer tank, said first and second electrodes are connected to said third and fourth electrodes.

8. Apparatus according to claim 2, further comprising means for directing bubbles produced by the flow of electrical current through the buffer solutions in said first and second reservoirs to the interface between said buffer tank and said support frame to thereby electrically isolate said first and second reservoirs from each other.

9. Apparatus according to claim 8, wherein said directing means comprise at least one sloped surface formed in the bottom of said support frame.

10. Apparatus according to claim 1, wherein said securing means comprise a restrainer removable, yet fastened to said support frame.

11. Apparatus according to claim 10, wherein said restrainer and said support frame act to secure the at least one gel slab in a substantially horizontal direction.

12. Apparatus according to claim 11, wherein said connecting means comprises a cover having third and fourth electrodes, wherein when said cover is positioned on said buffer tank, said first and second electrodes are connected to said third and fourth electrodes.

* * * * *